United States Patent [19]

Flisak et al.

[11] Patent Number: 5,663,368

[45] Date of Patent: Sep. 2, 1997

[54] SYNTHESIS OF ACID ADDITION SALTS OF HYDROXYLAMINES

[75] Inventors: Joseph R. Flisak, Lansdale; Stephen Torey Ross, Berwyn, both of Pa.

[73] Assignee: Smithkline Beecham Corporation, Philadelphia, Pa.

[21] Appl. No.: 581,562

[22] PCT Filed: Jul. 14, 1994

[86] PCT No.: PCT/US94/08117

§ 371 Date: Apr. 11, 1996

§ 102(e) Date: Apr. 11, 1996

[87] PCT Pub. No.: WO95/02574

PCT Pub. Date: Jan. 26, 1995

Related U.S. Application Data

[63] Continuation-in-part of Ser. No. 91,494, Jul. 14, 1993, abandoned.

[51] Int. Cl.$^6$ .............. C07D 333/66; C07D 307/82; C07D 311/58; C07D 209/88

[52] U.S. Cl. ............... 549/57; 549/1; 549/9; 549/23; 549/200; 549/355; 549/404; 549/439; 548/483; 546/160; 564/302; 540/476; 540/594

[58] Field of Search ............... 549/1, 9, 23, 57, 549/200, 355, 404, 439; 564/302; 548/483; 546/160; 540/476, 594

[56] References Cited

U.S. PATENT DOCUMENTS

| | | | |
|---|---|---|---|
| 1,390,260 | 9/1921 | Sulzberger | 260/132 |
| 2,132,454 | 10/1938 | Bassford | 260/130.5 |
| 3,118,933 | 1/1964 | Goldberg et al. | 260/501 |
| 3,163,677 | 12/1964 | Hoffman et al. | 260/583 |
| 4,983,771 | 1/1991 | Bryker et al. | 564/304 |
| 5,264,577 | 11/1993 | Beylin et al. | 546/136 |

OTHER PUBLICATIONS

Berge et al., J. Pharm. Sci., vol. 66, No. 1, pp. 1–19, (1977).

*Primary Examiner*—Jose G. Dees
*Assistant Examiner*—Mary C. Cebulak
*Attorney, Agent, or Firm*—Dara L. Dinner; Stephen Venetianer; Edward T. Lentz

[57] ABSTRACT

This invention relates to novel diastereomeric acid addition salts of homochiral hydroxylamines, to processes for obtaining such, to processes for the conversion thereof to the corresponding homochiral hydroxylamines, to certain novel homochiral hydroxylamines and the processes for using these as intermediates.

22 Claims, No Drawings

SYNTHESIS OF ACID ADDITION SALTS OF HYDROXYLAMINES

This application is a 371 of PCT/US94/08117 filed Jul. 14, 1994 which is a continuation-in-part of U.S. Ser. No. 08/091,494 filed Jul. 14, 1993 now abandoned.

This invention relates to novel diastereoisomeric acid addition salts of homochiral hydroxylamines, to processes for obtaining such, to processes for the conversion thereof to the corresponding homochiral hydroxylamines, to certain novel homochiral hydroxylamines and to processes for using these as intermediates.

Substituted hydroxylamines having an organic radical which has a chiral center will exist as a racemic mixture of the (+)- and (−)-enantiomers. For certain uses, such as a drug per se or as an intermediate in preparation thereof, it is increasingly important for regulatory purposes to be able to provide a single enantiomer, rather than the racemate. Accordingly, processes for obtaining such are being actively investigated.

In general, classical resolution techniques have taken advantage of the presence in the molecule of a functional group which may be used as a handle for the formation of a covalent or ionic bond. Thus, the racemic mixture may be reacted with a homochiral reagent to give a mixture of diastereoisomeric adducts which may then be separated by conventional techniques such as chromatography or fractional crystallization. The initial adduct forming reaction is then reversed on each of the isolated diastereoisomers, to yield the individual enantiomers. By way of example, a hydroxyl group in the compound of interest may be used to form an ester with a homochiral acid. Alternatively, if a suitable group is present in the compound of interest, ionic acid/base addition salts may be formed. Thus, a racemic amine may be treated with a homochiral acid (or vice versa) to form a pair of diastereoisomeric acid addition salts. More recently, use has been made of high performance liquid chromatography (hplc) in which the stationary phase is homochiral, thereby forming diastereoisomeric interactions in situ as the racemic material is eluted through the column.

In the past, it has been suggested that certain homochiral hydroxylamines may be obtained from homochiral precursors, for instance the corresponding homochiral amine or alcohol or via the intermediacy of diastereoisomeric adducts formed with, for instance, the N-chlorocarbonyl derivative of a homochiral oxazolidinone. See for example, PCT application no. WO 91/14774, (SmithKline Beecham) and the references cited therein.

We have now found that homochiral hydroxylamines may be obtained by a more direct process which does not involve the intermediacy of a covalently bonded diastereoisomeric adduct but instead takes advantage of the ability of a hydroxylamine to form acid addition salts. In particular, the combination of a racemic hydroxylamine and a homochiral organic acid will lead to the formation of a pair of diastereoisomeric acid addition salts. While such an approach has previously been used for amines, it has not yet, as far as we are aware, been applied to a hydroxylamine.

Accordingly, the present invention provides a diastereoisomeric acid addition salt of the formula (II):

[R*NHOZ][HA*]    (II)

in which R*NHOZ is an enatiometric hydroxylamine of the formula (I) wherein R* is an organic radical which contains a chiral carbon to which the NHOZ is attached, and Z is hydrogen or a hydroxyl protecting group; and HA* is a homochiral organic acid.

The asterisk * is used herein to denote chirality.

It will be appreciated that each of the homochiral hydroxylamines of formula (I) and the homochiral organic acid HA* may be either the (+)- or the (−)-enantiomer. It will be further appreciated that each diastereoisomeric salt of formula (II) may be one of four possible combinations viz. the (+)(+), (+)(−), (−)(+) and (−)(−) [(hydroxylamine)(acid)] combinations. This invention covers all such possibilities.

Suitable homochiral hydroxylamines of the formula (I) include homochiral organic radicals R* which contain a chiral carbon (C*) to which the hydroxylamine group NHOZ is attached and Z is as defined in relation to formula (I).

Examples of suitable such homochiral organic radicals (R*) of formula (I) include compounds of the formula (A):

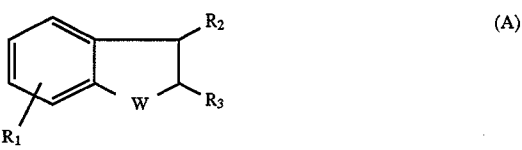

in which one of $R_2$ and $R_3$ is hydrogen; and the other is the chiral carbon (C*) to which the hydroxylmine group —NHOZ is attached;

W is $CH_2(CH_2)_s$, $O(CH_2)_s$, $S(CH_2)_s$, or $NR_4(CH_2)_s$;

$R_4$ is hydrogen, $(C_{1-4})$alkyl, phenyl, $(C_{1-6})$alkanoyl or aroyl;

s is a number having a value of 0 to 3, provided that when $R_2$ is hydrogen and W is $O(CH_2)_s$ or $S(CH_2)_s$, then s is 1 to 3 and when W is $NR_4(CH_2)_s$ then s is 1 to 3 and $R_3$ is hydrogen;

$R_1$ is selected from the group consisting of hydrogen, $(C_{1-10})$alkyl, $(C_{1-10})$alkoxy, naphthyl, $(CH_2)_m$—Ar—$(X)_v$, $(CH_2)_m(C=C)_n(CH_2)_p$—Ar—$(X)_v$, $O(CH_2)_m$Ar—$(X)_v$, $S(CH_2)_m$—Ar—$(X)_v$, or $N(CH_2)_m$—Ar—$(X)_v$;

p is a number having a value of 0 to 3;

m is a number having a value of 0 to 3;

n is a number having a value of 0 to 3;

v is a number having a value of 0 to 3;

Ar is selected from the group consisting of phenyl, naphthyl, quinolyl, isoquinolyl, pyridyl, furanyl, imidazoyl, benzimidazoyl, triazolyl, oxazolyl, isoxazolyl, thiazolyl, or thienyl;

X is a member selected from the group consisting of hydrogen, halogen, $(C_{1-10})$alkyl, $(C_{5-8})$cycloalkyl, $(C_{2-10})$alkenyl, hydroxy, carboxy(CHY)$_r$, $(C_{1-10})$alkoxy, $(C_{1-10})$alkylthio, $(C_{1-10})$alkylsulphinyl, $(C_{1-10})$alkylsulphonyl, aryloxy, aryl($C_{1-6}$)alkyloxy, halo($C_{1-6}$)alkyl, hydroxy($C_{1-6}$)alkyl, $(R_5)_2N(CHY)_r$, or cyano; provided that if v is a number greater than 1, then one substituent must be selected from alkyl, $(C_{1-10})$alkoxy or halo; t is 0 or 1;

$R_5$ is hydrogen or $(C_{1-6})$alkyl;

Y is hydrogen or $(C_{1-3})$alkyl;

t' is 0 or 1; and if t' is 1 than one of $R_5$ must be hydrogen;

or a salt, preferably a pharmaceutically acceptable salt, thereof;

and compounds of formula (B):

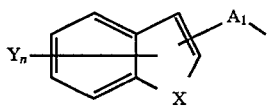

wherein $A_1$ contains a C* (chiral carbon adjacent to hydroxylamine group);

$A_1$ is a $C_{1-6}$ alkylene or $C_{2-6}$ alkenylene group;

Y is selected independently at each occurrence from hydrogen, halogen, hydroxy, cyano, halosubstituted alkyl, $C_{1-12}$ alkyl, $C_{2-12}$ alkenyl, $C_{1-12}$ alkoxy, $C_{3-8}$ cycloalkyl, $C_{1-12}$ thioalkyl, aryl, aryloxy, aroyl, $C_{1-12}$ arylalkyl, $C_{1-12}$ arylalkenyl, $C_{1-12}$ arylalkoxy, $C_{1-12}$ arylthioalkoxy and substituted derivatives of aryl, aryloxy, aroyl, $C_{1-12}$ arylalkyl, $C_{2-12}$ arylalkenyl, $C_{1-12}$ arylalkoxy, $C_{1-12}$ arylthioalkoxy wherein substituents are selected from halo, nitro, cyano, $C_{1-12}$ alkyl, alkoxy, and halosubstituted alkyl;

n is 1to 5;

X is oxygen, sulfur, $S(O)_2$ or $NR_1$;

$R_1$ is hydrogen, $C_{1-6}$ alkyl, $C_{1-6}$ alkanoyl, aroyl, or alkylsulfonyl;

the dotted line within the five membered ring signifies a single or double bond;

or a salt, preferably a pharmaceutically acceptable salt thereof;

and compounds of formula (C):

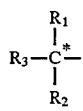

wherein:

$R_3$ is $A_1$—$R_4$—;

$A_1$ is $C_{5-20}$ alkyl, cycloalkyl, aryl, aryloxy, arylcycloalkyl, aryloxy alkyl, arylalkoxyalkyl, arylthioalkyl, Aryl NH-alkyl, N-Aryl-N-(alkylkamino alkyl), N-(Arylalkylamino alkyl), N-(Aryl-alkyl)-N-(alkyl amino) alkyl, heteroaryl, heteroarylalkyl, heterocyclyl, heterocyclyl alkyl;

$R_4$ is a bond, $C_{1-6}$ alkylene, $C_{2-6}$ alkenylene, $C_{2-6}$ alkynylene, aryl, heteroaryl, or $C_{3-8}$ cycloalkyl;

$R_1$ and $R_2$ are hydrogen, $C_{1-4}$ alkyl, aryl, arylalkyl, heteroaryl, heteroarylalkyl, heteocyclyl, heterocyclylalkyl, or $C_{3-8}$ cycloalkyl; provided that $R_1$, $R_2$ and $R_3$ are not the same;

C* denotes the chiral carbon to which the hydroxylmine group (NHOZ) is attached; or a salt, preferably a pharmaceutically acceptable salt, thereof.

For compounds within the scope of formula (B) and (C) the "alkylene", "alkenylene", "alkynyl" chain as used herein may mean a straight or branched chain. Such groups include —CHCH$_3$—, CH(CH$_2$CH$_3$)—, CH$_2$CH$_2$(CH$_3$)—, CH$_2$CH$_2$ (CH$_2$CH$_3$)—, and the like, —CH=CH—, CH=CHCH— (CH$_3$), —C(CH$_3$)=CH— and the like. A preferred group is —CHCH$_3$—. For the compounds of Formula (B) and (C), the four groups on the carbon directly attached to the hydroxylamine moiety must be direct so that the resulting compound is chiral.

As indicated in the structure for Formula (C) the $R_1$, $R_2$ and $R_3$ terms must be different, preferably $R_3$ is a $A_1$—$R_4$ wherein $R_4$ is a $C_{2-6}$ alkynyl group, $C_{2-6}$ alkylene, or a $C_{2-6}$ alkenylene group. More preferably $C_{2-6}$ alkynyl, or a $C_{2-6}$ alkenylene group. Most preferably a $C_2$ alkynyl. Preferably one of $R_1$ and $R_2$ is hydrogen and the other a $C_{1-12}$ alkyl, more preferably methyl.

In Formula (C) when $A_1$ is a heteroaryl, the heteroaryl is preferably selected from an optionally substituted 2- or 3-furanyl, optionally substituted 2- or 3-thienyl, optionally substituted benzo(b)furyl, or optionally substituted benzo(b) thienyl. Preferably, when $A_1$ is aryl it is an optionally substituted phenyl or naphthyl ring.

A preferred substructure of Formula (C) is wherein $A_1$ is optionally substituted phenyl, optionally substituted naphthyl, optionally substituted 2- or 3-furanyl, or optionally substituted 2- or 3-thienyl; and preferably $R_1$ and $R_2$ are independently hydrogen, or $C_{1-6}$alkyl, aryl, heteroaryl or $C_{3-8}$ cycloalkyl.

Preferred optional substituents for the $A_1$ moieties are as described in WO 92/01682 published 6 Feb. 1992 (Brooks et al.) whose disclosure is hereby incorporated by reference. More preferably the substituents are an optionally substituted aryl, or aryloxy. The preferred substituents on the aryl or aryloxy are independently, halogen, haloalkyl, alkoxy, alcohol or alkyl. More preferably halogen, specifically one or more fluorines.

Compounds within the scope of formula (A) are disclosed in PCT publication WO91/14774 (SmithKline Beecham) the disclosure of which is incorporated herein by reference. Compounds of formula (B) are disclosed in U.S. Pat. No. 4,873,259 (Summers et al.) the disclosure of which is incorporated herein by reference. Compounds of formula (C) are disclosed in WO 92/01682, published 6 Feb. 1992 (Brooks et al.) whose disclosure is hereby incorporated by reference. Additionally, compounds within the scope of Formula (C) are disclosed in EPO 0 384 594 A, published 19.08.90 (Wellcome Foundation) whose disclosure is also incorporated by reference herein in its entirety.

Preferably within the compounds of formula (A), $R_1$ is selected from $O(CH_2)_m$—Ar—$(X)_v$, $(CH_2)_m$—Ar—$(X)_v$, or $S(CH_2)_m$—Ar—$(X)_v$; m is a number having a value of 0 to 3; and v is a number having a value of 1 to 2. Preferably Ar is phenyl. Preferred X groups are hydrogen, alkoxy, halo, and $CF_3$, preferably in the 4-position. More preferably, X is hydrogen, or halogen, preferably fluoro or chloro, more preferably fluoro. When disubstituted, the ring is preferably substituted by halogen, preferably in the 2,6-position. More preferably, X is fluoro or chloro, more preferably di-fluoro.

Specific $R_1$ groups of interest for compounds of Formula (I) are alkoxy, phenethyl, benzyloxy, phenoxy and substituted derivatives thereof. Specifically such groups are methoxy, phenoxy, benzyloxy, 4-methoxylbenzyloxy, 4-chlorobenzyloxy, 4-fluorophenoxy, 2,6-difluorobenzyloxy, 2-phenylethyl, 2-quinoylmethoxy, and 2-naphthylmethoxy. Preferably, W is $CH_2(CH_2)_s$ or $O(CH_2)_s$ and s is a number having a value of 0 or 1. Preferably $R_3$ is hydrogen. A preferred ring placement when W is $CH_2(CH_2)_s$ and s is 1 is on the 5- or 6-position of the benzofuran ring and when s is 0 the preferred position is the 4- or 5-position; corresponding substitution patterns are also preferred when W is $O(CH_2)_s$, i.e., when s is 1, the 7- or 8-position, and when s is 0 the 6- or 7-position.

Preferably within the compounds of formula (B), A is —CH$_2$— or —C(CH$_3$)H—; X is sulfur or oxygen; the dotted line is a double bond, and the Y term is hydrogen. More preferably $A_1$ is C(CH$_3$)H and X is sulfur.

Preferably within the compounds of formula (C), $R_1$ is independently hydrogen or methyl; more preferably one of $R_1$ is hydrogen and the other is methyl; $A_1$ is an optionally substituted aryl or optionally substituted 2- or 3-furanyl. More preferably $A_1$ is a 2-furanyl substituted by an optionally substituted phenoxy group. The phenoxy group is optionally substituted preferably by halogen, more preferably fluorine and more preferably in the 4-position. As U.S. Pat. No. 4,873,259 (Summers et al.) and WO 92/01682, published 6 Feb. 1992 (Brooks et al.) are incorporated herein by reference in their entirety the list of optional substituents disclosed therein for the compounds of Formula (IB) and (IC) will not be defined in greater detail herein.

Examples of suitable homochiral organic acids HA* include mild organic acids selected from among the homochiral acids conventionally used as resolving agents for racemic amines, for instance a dibasic acid such as (+)/(2R, 3R)- or (−)/(2S,3S)-tartaric acid or a derivative thereof such as dibenzoyl-(2S,3S)- or (2R,3R)-tartaric acid or, more preferably, a monobasic acid such as (S)-(+)- or (R)-(−)- mandelic acid $[C_6H_5CH(OH)CO_2H]$. Mono derivatives of tartaric acid (or other dibasic acids) such as the mono esters or amides may also be used, similarly the derivatives of mandelic acid substituted on the benzylic hydroxyl group may also be used. Stronger organic acids such as camphorsulphonic acid should preferably be avoided. Suitable homochiral organic acids are readily available from the normal commercial suppliers. The organic acid should be a substantially pure homochiral enantiomer. It is preferable that the organic acid be at least 95% chirally pure or better, more preferably 97% or better, most preferably better than 99% pure.

The term "hydroxyl protecting group" is used herein to describe those groups well known in the art which may used to protect a hydroxyl group and which may be added to and removed from the substrate molecule without disturbing the remainder of the molecule. Suitable examples thereof are given in "Protecting Groups in Organic Chemistry", Greene T. W., Wiley, New York, 1981. Preferred values for the hydroxyl protecting group Z include optionally substituted benzyl, methyl($C_{1-3}$)alkoxy, methylethoxy($C_{1-3}$)alkoxy, lower alkoxycarbonyl, tetrahydropyranyl, lower alkanoyl, aroyl, trialkylsilyl and trialkylsilylethoxymethyl.

The terms "aryl" or "heteroaryl" are used herein and unless otherwise defined to mean substituted and unsubstituted aromatic ring(s) or ring systems containing from 5 to 16 carbon atoms, which may include bi- or tri-cyclic systems and may include, but are not limited to, heteroatoms selected from O, N, or S. Representative examples include, but are not limited to, phenyl, naphthyl, pyridyl, quinolinyl, thiazinyl, 2- or 3-thienyl and 2- or 3-furanyl, benzo(b)furyl or benzo(b)thienyl.

The terms "lower alkyl" or "alkyl" are used herein and unless otherwise defined to mean straight or branched chain radicals of 1 to 10 carbon atoms, unless the chain length is otherwise limited, including, but not limited to methyl, ethyl; n-propyl, iso-propyl, n-butyl, sec-butyl, iso-butyl, tert-butyl, and the like.

The term "aroyl" is used herein to mean ArC(O)—, in which Ar is as defined in Formula (A), including, but not limited to benzyl, 1- or 2-naphthyl and the like.

The term "alkanoyl" is used herein to mean $(C_{1-10})C(O)$ —, in which alkyl is as defined above, including but not limited to methyl, ethyl, isopropyl, n-butyl, t-butyl, and the like.

The term "cycloalkyl" is used herein to mean cyclic radicals, preferably of 3 to 8 carbons, including but not limited to cyclopropyl, cyclopentyl, cyclohexyl, and the like.

The skilled person will appreciate that for any given racemic hydroxylamine, some homochiral organic acids will be more effective as resolving agents than others. Suitable combinations will be readily determined by the skilled man by simple experiment, the preferred combinations being those which allow for more effective purification of the diastereoisomeric acid addition salts.

Examples of suitable diastereoisomeric acid addition salts of formula (I) include:

(S)-N-(6-benzyloxy-2,3-dihydrobenzofuran-3-yl) hydroxylamine (S)-mandelate;
(R)-N-(6-benzyloxy-2,3-dihydrobenzofuran-3-yl) hydroxylamine (S)-mandelate;
(S)-N-(6-benzyloxy-2,3-dihydrobenzofuran-3-yl) hydroxylamine (R)-mandelate;
(R)-N-(6-benzyloxy-2,3-dihydrobenzofuran-3-yl) hydroxylamine (R)-mandelate;
(S)-N-(6-[2,6-difluoro-benzyloxy]-2,3-dihydrobenzofuran-3-yl)hydroxylamine (S)-mandelate;
(R)-N-(6-[2,6-difluoro-benzyloxy]-2,3-dihydrobenzofuran-3-yl)hydroxylamine (S)-mandelate;
(S)-N-(1-benzo[b]thien-2-yl-ethyl)hydroxylamine (S)-mandelate;
(R)-N-(1-benzo[b]thien-2-yl-ethyl)hydroxylamine (S)-mandelate.
(S)-N-(1-benzo[b]thien-2-yl-ethyl)hydroxylamine (R)-mandelate;
(R)-N-(1-benzo[b]thien-2-yl-ethyl)hydroxylamine (R)-mandelate;
(S)-N-(4-[5-(4-Fluorophenoxy)-2-furyl]-3-butyn-2-yl] hydroxylamine (S)-mandelate;
(R)-N-(4-[5-(4-Fluorophenoxy)-2-furyl]-3-butyn-2-yl] hydroxylamine (S)-mandelate;
(S)-N-(4-[5-(4-Fluorophenoxy)-2-furyl]-3-butyn-2-yl] hydroxylamine (R)-mandelate; or
(R)-N-(4-[5-(4-Fluorophenoxy)-2-furyl]-3-butyn-2-yl] hydroxylamine (R)-mandelate.
(E)-N-3[3-(4-Flurophenoxy)phenyl-1-methyl-prop-2-en-1-yl]hydroxylamine (S)-mandelate;
(E)-N-3[3-(4-Flurophenoxy)phenyl-1-methyl-prop-2-en-1-yl]hydroxylamine (R)-mandelate;

Alternate nomenclature for the (4-[5-(4-Fluorophenoxy)-2-furyl]-3-butyn-2-yl] moiety is 3-[5-(4-Fluorophenyl)-2-furanyl]-1-methyl-2-propanyl.

While the diastereoisomeric acid addition salt of formula (I) may be trivially formed by treating the corresponding homochiral hydroxylamine with a homochiral organic acid HA*, it will be readily appreciated that more usually the salt will be obtained as an intermediate product in the resolution of the corresponding racemic hydroxylamine. Thus the more usual starting material will be the corresponding racemic hydroxylamine. In addition, a further useful starting material may be the partially resolved hydroxylamine which may have been obtained as a result of a previous incomplete attempt to resolve the hydroxylamine via, for instance, the formation of the same or a different diastereoisomeric acid addition salt.

Accordingly, the present invention further provides a process for preparing a diastereoisomeric acid addition salt of formula (I) as hereinbefore defined which process comprises treating the corresponding racemic or partially resolved hydroxylamine with a homochiral organic acid HA* in a suitable solvent, such as alcohols or ethyl acetate, to form a pair of diastereoisomeric acid addition salts which may then be separated by any suitable means, for instance fractional crystallization.

Preferably, substantially equivalent amounts of the hydroxylamine and the organic acid are employed. If the organic acid is dibasic, then preferably a monohydrogen salt is formed. Preferably, the organic acid is mandelic acid. While a 1:1 ratio is preferable a 2:1 ratio has also been successful in this process.

Suitable solvents include those normally used in acid addition salt formation, such as ethyl acetate, acetonitrile, acetone, or an alcohol optionally with acetic acid, for instance methanol, ethanol or isopropanol, preferably methanol or ethanol, and more preferably methanol with acetic acid. Preferably the solvents are ethyl acetate or methanol with acetic acid.

Preferably, a solvent is selected such that following initial salt formation, one of the diastereoisomeric salts selectively precipitates out, thereby effecting at least partial separation. Alternatively, it may be preferred to either wholly or partially replace the initial salt formation solvent by another, to allow more effective separation by fractional crystallization.

Preferably, salt formation is carried out with efficient stirring and temperature control, so that, if a suitable solvent is chosen, fractional crystallization may occur in a controlled fashion.

The skilled person will appreciate that substantially complete separation of the diastereoisomeric acid addition salts may not be achieved in a single step and that accordingly it may be necessary to process the impure salt through further separation steps until the desired level of purity is obtained. If fractional crystallization is being used, this may involve changing solvent from that used in the initial salt forming step. The diastereoisomeric purity of the salt may be readily monitored through physical parameters such as the melting point of the salt or by use of $^1$H nmr spectroscopy. Alternatively, the free hydroxylmine may be generated from the salt and the optical rotation thereof measured or it may be assayed by hplc using achiral stationary phase or by $^1$H nmr spectroscopy using a chiral shift reagent. Optimization of the crystallization step herein, such as by seeding the solution with the preferred diasteriomeric form may allow for direct crystallization as opposed to recrystallization.

Diastereoisomeric salts of formula (I) are of use as intermediates in the preparation of the corresponding homochiral hydroxylamines.

Accordingly, in a further aspect the present invention provides a process for preparing a homochiral hydroxylmine of the formula (I) as hereinbefore defined [R*NHOZ], or a salt thereof, which process comprises treating a diastereoisomeric salt of formula (II), as hereinbefore defined [R*NHOZ][HA*], with a suitable base in a suitable solvent and preferably with control of pH and temperature, to generate the corresponding homochiral hydroxylamine which may then be separated from the organic acid, as hereinbefore defined [HA*] by extraction into a suitable organic solvent. Another advantageous aspect of the present invention is the recovery of the homochiral acid in this process, allowing for reduced costs as the acid can be reused.

Suitable bases include mild amine bases such as aqueous ammonium hydroxide. Suitable solvents include water.

It will be appreciated that within the compounds of formula (II) there exists a subset of compounds which are novel and also useful as intermediates.

Accordingly, in a further aspect the present invention provides homochiral hydroxylamines of the formula (III):

(R*)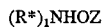NHOZ  (III)

in which Z is as defined for Formula (I) and a) (R*)$_1$ is a homochiral organic radical of the formula:

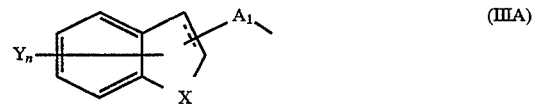

(IIIA)

wherein A$_1$ contains the C* (chiral carbon adjacent to hydroxylamine group);

A$_1$ may be a C$_{1-6}$ alkylene or C$_{2-6}$ alkenylene group;

Y is selected independently at each occurrence from hydrogen, halogen, hydroxy, cyano, halosubstituted alkyl, C$_1$–C$_{12}$ alkyl, C$_2$–C$_{12}$ alkenyl, C$_1$–C$_{12}$ alkoxy, C$_3$–C$_8$ cycloalkyl, C$_1$–C$_{12}$ thioalkyl, aryl, aryloxy, aroyl, C$_1$–C$_{12}$ arylalkyl, C$_1$–C$_{12}$ arylalkenyl, C$_1$–C$_{12}$ arylalkoxy, C$_1$–C$_{12}$ arylthioalkoxy and substituted derivatives of aryl, aryloxy, aroyl, C$_1$–C$_{12}$ arylalkyl, C$_2$–C$_{12}$ arylalkenyl, C$_1$–C$_{12}$ arylalkoxy, C$_1$–C$_{12}$ arylthioalkoxy wherein substituents are selected from halo, nitro, cyano, C$_1$–C$_{12}$ alkyl, alkoxy, and halosubstituted alkyl;

n is 1 to 5;

X is oxygen, sulfur, S(O)$_2$ or NR$_1$;

R$_1$ is hydrogen, C$_{1-6}$ alkyl, C$_{1-6}$ alkanoyl, aroyl, or alkylsulfonyl;

the dotted line within the five membered ring signifies a single or double bond;

or a salt, preferably a pharmaceutically acceptable salt thereof; or b) in which (R*)$_1$ is a homochiral organic radical of the formula:

(IIIB)

wherein:

A$_1$ is C$_{5-20}$ alkyl, cycloalkyl, aryl, aryloxy, arylcycloalkyl, aryloxy alkyl, arylalkoxyalkyl, arylthioalkyl, Aryl NH-alkyl, N-Aryl-N-(alkylkamino alkyl, N-(Arylalkylamino alkyl), N-(Aryl-alkyl)-N-(alkyl amino) alkyl, optionally substitued 2- or 3-furyl, optionally substituted 2- or 3-thienyl, optionally substitued benzo (b)furyl, or optionally substituted benzo(b)thienyl;

R$_1$ is hydrogen or C$_{1-2}$ alkyl;

or a salt, preferably a pharmaceutically acceptable salt thereof.

Examples of such suitable homochiral (R*)$_1$ moieties include:

(+)- and (−)-N-3-(6-benzyloxy-2,3-dihydrobenzofuryl);

(+)- and (−)-N-[4-[5-(4-fluorophenoxy)-2-furyl]-3-butyn-2-yl]; or (+)- and (−)-N-3-(6-[2,6-difluorobenzyloxy]-2,3-dihydrobenzofuryl).

Examples of the resulting suitable homochiral hydroxylamines from formulas (IIIA) and (IIIB) include:

(S)-N-(6-benzyloxy-2,3-dihydrobenzofuran-3-yl) hydroxylamine;

(R)-N-(6-benzyloxy-2,3-dihydrobenzofuran-3-yl) hydroxylamine;

(S)-N-(6-[2,6-difluorobenzyloxy]-2,3-dihydrobenzofuran-3-yl)hydroxylamine;

(R)-N-(6-[2,6-difluorobenzyloxy]-2,3-dihydrobenzofuran-3-yl)hydroxylamine;

(+)- and (−)-N-[4-[5-(4-fluorophenoxy)-2-furyl]-3-butyn-2-yl]hydroxylamine.

Homochiral hydroxylamines of formula (IIIA) and (IIIB) may be obtained as hereinbefore described for homochiral hydroxylamines of formula (I).

Homochiral hydroxylamines may be usefully used as intermediates in the preparation of inter alia the corresponding homochiral hydroxyurea and hydroxamate derivatives.

Accordingly, in a further aspect the present invention provides a process for preparing a homochiral compound of the formula (IV):

$(R^*)_1N(OZ)CY_1R_6$     (IV)

in which $(R^*)_1$ is as defined in relation to formula (IIIA) and (IIIB), and Z is as defined in formula (I);

$Y_1$ is oxygen or sulfur;

$R_6$ is $(C_{1-6})$alkyl, halosubstituted$(C_{1-6})$alkyl, hydroxy substituted$(C_{1-6})$alkyl, $(C_{2-6})$alkenyl, aryl or heteroaryl optionally substituted by halogen, $(C_{1-6})$alkyl, halosubstituted$(C_{1-6})$alkyl, hydroxyl or $(C_{1-6})$alkoxy; or $R_6$ is the group $NR_7R_8$;

$R_7$ is hydrogen or $(C_{1-6})$alkyl;

$R_8$ is hydrogen, $(C_{1-6})$alkyl, aryl$(C_{1-6})$alkyl, $(C_{1-6})$alkyl substituted by halogen or hydroxyl, aryl or heteroaryl optionally substituted by a substituent selected from the group consisting of halo, nitro, cyano, $(C_{1-12})$alkyl, $(C_{1-6})$alkoxy, halo$(C_{1-6})$alkyl, $(C_{1-6})$alkoxycarbonyl, aminocarbonyl, $(C_{1-6})$alkylaminocarbonyl, di$(C_{1-6})$alkylaminocarbonyl, $(C_{1-6})$alkylthio, $(C_{1-6})$alkylsulphinyl or $(C_{1-6})$alkylsulphonyl; or $R_7$ and $R_8$ may together form a ring having 5 to 7 ring atoms, which ring atoms may optionally include a further heteroatom selected from oxygen, sulfur or nitrogen;

or a salt thereof, preferably a pharmaceutically acceptable thereof;

which process comprises treating a homochiral hydroxylamine of formula (III) as hereinbefore defined with a reagent capable of transforming a hydroxylamine functional group into a hydroxyurea or a hydroxamate.

Such reagents are well known in the art and include those described in U.S. Pat. No. 4,873,259 (Summers et al). Useful reagents include trimethyl silyl isocyanate, alkali metal cyanate, phosgene or a phosgene equivalent followed by ammonia or an amine (for a hydroxyurea) or an acylating agent such as an acyl chloride or an acid anhydride (for a hydroxamate).

In more detail, suitable processes for preparing a hydroxyurea of formula (IV) include treating a compound of formula (III) as described above in which Z is hydrogen or a hydroxyl protecting group, with:

(i) trimethylsilyl isocyanate, followed by work up with ammonium chloride;

(ii) sodium or potassium cyanate in an acidic solution; or (iii) gaseous hydrogen chloride, followed by phosgene or a phosgene equivalent (to give the corresponding carbamoyl chloride intermediate) or an alkylchloroformate, such as ethyl chloroformate (to give the corresponding carbamate intermediate) and then treating the intermediate with aqueous ammonia or a substituted amine; and then if necessary and so desired, removing the protecting group Z.

Suitable processes for preparing a hydroxamate of formula (IV) include treating a compound of formula (III) as described above in which Z is hydrogen or a hydroxyl protecting group, with an acylating agent such as an acyl chloride, for instance acetyl chloride, or an acid anhydride in an organic solvent and optionally in the presence of a base and thereafter and if necessary, removing the protecting group.

Suitable examples of protecting groups Z for use in compounds of the formula (I), (II), (III), and (IV) in the above processes, with methods for the cleavage thereof in parenthesis, include:

(i) benzyl, substituted benzyl or a benzyl carbonate (hydrogenolysis or with ethane thiol in the presence of aluminium trichloride);

(ii) trialkylsilyl or trialkylsilylethoxymethyl (anhydrous amine fluoride or mildly acidic conditions);

(iii) tetrahydropyranyl, $(C_{1-3})$alkoxy$(C_1)$alkyl or $(C_{1-3})$alkoxy$(C_2)$alkoxy-$(C_1)$alkyl (mild acid treatment, such as pyridinium 4-toulenesulphonate in methanol or dilute HCl);

(iv) t-butyloxycarbonyl (trifluroracetic acid, trimethylsilyltriflate with 2,6-lutidine, or anhydrous ethereal HCl); and (v) a lower alkanoyl or aroyl group (suitable base, such as potassium carbonate).

This invention will now be described by way of the following examples which are merely for the purposes of illustration and in no way intended to limit the scope of the invention.

EXAMPLE 1

(R)-N-Hydroxy-N-(1-benzo[b]thien-2-yl-ethyl)urea a). (R)-N-Hydroxy-N-(1-benzo[b]thien-2-yl-ethyl)amine (S)-mandelate

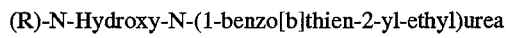

20.0 g (0.103 mole) of racemic N-hydroxy-N-(1-benzo[6]thien-2-yl-ethyl)amine and 200 ml of MeOH (heated on the steam bath), followed by a solution of 15.75 g of (S)-(+)-mandelic acid in 25 ml of MeOH (added all at once). Heated with stirring an additional 5 minutes, then allowed to slowly cool to R.T. (overnight), chilled in an ice bath 1 hr, filtered, collected and dried to give 5.13 g (14.4% yield) of the (R)-hydroxylamine (S)-(+)-mandelate. TLC one spot, chiral HPLC greater than 99%.

b). (R)-N-Hydroxy-N-(1-benz[b]thien-2-yl-ethyl)amine 5.13 g of the (R)-hydroxylamine (S)-(+)-mandelate salt taken up in EtOAc, water added, cooled, followed by addition of conc. $NH_4OH$ with stirring to pH~9.0. Layers separated, and the aqueous extracted with EtOAc (2×). EtOAc combined, washed with water, dried, and concentrated on the roto-vap to give 2.72 g (13.6% yield) from racemic mixture starting material. Chiral HPLC greater than 99%; TLC one spot. Mp.=107°–8° C.

c). (R)-N-Hydroxy-N-(1-benzo[6]thien-2-yl-ethyl)urea 2.72 g (0.014 mole) of (R)-N-Hydroxy-N-(1-benzo[b]thien-2-yl-ethyl)amine and 27 ml of THF, followed by 3.0 ml (0.021 mole) of TMS isocyanante and heated to reflux for 0.5 hr, cooled to 5° C. in an ice bath and the resultant solid filtered off. The filtrate concentrated, taken up in a minimum of DMF, decolorized with activated carbon, Darco®, treated with ice and the resultant solid collected and dried, and combined with above to give 2.9 g crude hydroxyurea. Material recrystallized from $CH_3CN$ (2×) to give 1.71 g (51.7% yield). HPLC: 99.4% [a]D=+50.7° (C=1.7, MeOH, 25° C.); Mp.=156°–8° C.

EXAMPLE 2

(S)-N-Hydroxy-N-(1-benzo[b]thien-2-yl-ethyl)urea a). (S)-N-Hydroxy-N-(1-benzo[b]thien-2-yl-ethyl)amine (R)-mandelate 16.7 g (0.086 mole) of racemic N-Hydroxy-N-(1-benzo[b]thien-2-yl-ethyl)amine and 167 ml of MeOH (heated on the steam bath), followed by a solution of 13.15 g (0.086 mole) of (R)-(–)-mandelic acid in 25 ml of MeOH (added all at once). Heated with stirring an additional 5 minutes, then allowed to slowly cool to R.T. (overnight), chilled in an ice bath one hr., filtered, collected, and dried to give 13.15 g (44.3% yield) of the (S)hydroxylamine(R)-(–)-mandelate. TLC one spot, chiral HPLC greater than 99%.

b). (S)-N-Hydroxy-N-(1-benzo[b]thien-2-yl-ethyl)amine 13.15 g (0.038 mole) of the (S)Hydroxylamine(R)-(–)-mandelate salt taken up in EtOAc, water added, cooled, followed by addition of conc. $NH_4OH$ with stirring to pH~9.0. Layers separated, and the aqueous extracted with EtOAc (2×). EtOAc combined, washed with water, dried, and concentrated on the roto-vap to give 5.5 g of the (S)Hydroxylamine, (32.9% yield) from the racemic starting material. Chiral HPLC greater than 99%; TLC one spot. Mp.=110°–111° C.

c). (S)-N-Hydroxy-N-(1-1-benzo[b]thien-2-yl-ethyl)urea 5.25 g (0.027 mole) of (S)-N-Hydroxy-N-(1-benzo[6]thien-2-yl-ethyl)amine and 53 ml of THF, followed by 5.8 ml (0.041 mole) of TMS isocyanate and heated to reflux for 0.5 hr, cooled rapidly to 5° C. in an ice bath and the resultant solid filtered off. The filtrate concentrated and the residue taken up in a minimum of DMF, decolorized with activated carbon, Darco®, treated with ice and the resultant solid collected, dried and combined with above to give the crude hydroxyurea. Recrystallized from $CH_3CN$ (2×) to give 3.01 g (47.2% yield). HPLC: 99.1%; $[\alpha]_D^{25°}$=50.7° (C=1.7, MeOH); Mp.=158°–160° C.

EXAMPLE 3

(S) N-[6-Benzyloxy-2,3-dihydrobenzofuran-3-yl]-hydroxylamine a) Resolution Of Hydroxylamine via D-Tartrate Salt A portion of 6-Benzyloxy-3-(N)-hydroxylamino-2,3-dihydrobenzofuran (0.88 g) was dissolved in 30 ml. MeOH with heating, the solution cooled somewhat and a solution of (0.514 g.) D-(S,S) tartaric acid in 10 ml MeOH was added in one portion with stirring. Rapid crystallization occurred, and the solid and supernatant were stored overnight at ca 5°, then filtered and air-dried (yield 1.6 g). This was stirred with 20 ml. AcOH and the mixture heated to 65°–70° at which point a complete solution occurred. The solution was chilled to ca 10° and scratched to give a crystalline solid. After stirring a few minutes the solid was filtered and air dried to give 314 mg (45%) of first crop material. m.p. 169°–170° dec. Second crop-70 mg (10%) m.p. 166°–168° dec.

A 19 mg portion of the first crop was dissolved in aq. $NH_4OH$ containing some MeOH and the solution was extracted with EtOAc. Conc. of ethyl acetate extracts give 12 mg of solid residue. Assay by chiral HPLC-Chiralpak AD (amylose) column 25 cm. mobile phase 90% Hexane, 10% $(CH_3)_2CHOH$, flow rate 1 ml/min. Results: 25.2 min–(95%, 30.7 m–4.1% (91.8% e.e.) [α]25°+18.6°) Estimated $[\alpha]_D^{25°}$ 100% e.e. material: (+)20.3°.

b) Conversion Of Hydroxylamine to Hydroxyurea

A portion of (S)-6-Benzyloxy-3-(N)-hydroxylamino-2,3-dihydrobenzofuran, (ca 10 mg) was dissolved in ca 0.5 ml of THF (seive-dried) and ca. 50 µl trimethylsilyl isocyanate (excess) was added. The reaction mixture was stirred at ambient temp. under argon over two days during which time the mixture went to dryness. The white residual solid was triturated with THF and the solid filtered (3 mg) m.p. sl. dec>190° Chiral HPLC showed this product to be identical to (S) N-[6-Benzyloxy-2,3-dihydrobenzofuran-3-yl]hydroxyurea: Chiracel OJ 4.6 mm×25 cm column, 60% hexane, 40% EtOH isochratic mobile phase, flow rate 1 ml/min (210 nm) S-17.9 m, (R-12.1 m, no peak).

Under alternative conditions:

c) (S)-Hydroxylamine Conversion to (S)-Hydroxyurea

A portion of (S)-6-Benzyloxy-3-(N)-hydroxylamino-2,3-dihydrobenzofuran (1.4 g) was stirred in 15 ml THF at ambient temp. under argon (solid form of powder and lumps-fairly insoluble) in trimethylsilylisocyanate (1.11 ml) was added in a single portion. An immediate white precipitate formed which became heavy and restricted stirring lumps of starting material still evident. An additional 15 ml. of THF was added and the reaction mixture was heated to reflux. Reaction mixture gradually became of smooth consistency but insoluble white material remained. Reaction mixture was refluxed for 1 hour and then was cooled and filtered to give a white solid, 1.31 g (80%). Reverse phase HPLC-Rainin. Grad. Zorbax 4.6 mm×15 cm column, RX $C_8$, 50% MeOH, 0.1% TFA (aq.) (5 min) 10 min to 90% MeOH, 0.1% TFA/aq.) (10 min.), flow rate 1 ml/min; single peak (ca 100%) 10.7 min. Chiral HPLC assay: Chiracel OJ/4.6 mm×25cm column 40% EtOH:60% Hexane isochratic, 1 ml/min, UV 210 nm Single peak 18.3 min (S-enant.). (R enant. 12.3 min-no peak) m.p. 190°–194° C. dec. $^1$HNMR & $^{13}$CNMR spectra obtained $(CD_3)_2SO$ (Gaspe)-consistent. Mass spectrum (PI)-301 (Daltons)-consistent.

A sample (37 mg) of the reaction product was triturated with EtOH (reflux) to give 33 mg of crystalline solid. Sample vacum dried. Calc'd for $C_{16}H_{16}N_2O_4$: C, 63.99; H, 5.37; N, 9.33. Found: C, 63.86; H, 5.30; N, 9.15. $[\alpha]_D^{25°}$ (1, DMF)+90.2°.

EXAMPLE 4

(S)-N-[6-Benzyloxy-2,3-dihydrobenzofuran-3-yl] hydroxylamine.

To a 22 L. flask equipped with a mechanical stirrer, thermometer and reflux condenser was placed (R,S)-N-[6-benzyloxy-2,3-dihydrobenzofuran-3-yl]hydroxylamine (551.0 g, 2.14 mol) in MeOH (17 L), and the resulting mixture was heated to reflux. To the refluxing mixture was added all at once a solution of(S)-(+)-mandelic acid (325.8 g, 2.14 mol) in MeOH (0.5 L). Heating was continued for 5 min, then the mixture was allowed to slowly cool. When the temperature reached 50° C., a seed crystal was added to the mixture, and the solid which formed was collected by filtration and dried. HPLC analysis of the collected solid showed it to contain 85:15 (S):(R)-N-[6-benzyloxy-2,3-dihydrobenzofuran-3-yl]hydroxylamine. The solid (513.6 g) was placed in a 22 L flask containing EtOAc (12 L), then was stirred and heated at 70° C. for 0.5 h and slowly allowed to cool. When the temperature reached 50° C., a seed crystal was added to the mixture, and the solid which formed was collected by filtration and dried. HPLC analysis of the collected solid showed it to contain >99% (S)-N-[6-benzyloxy-2,3-dihydrobenzofuran-3-yl]hydroxylamine. The solid was placed in a 22 L separatory flask to which was added cold H2O (3 L) and EtOAc (6 L). The pH was adjusted to pH 9 by the addition of conc. $NH_4OH$. The layers were separated, and the aqueous phase was extracted with EtOAc (2×2 L). The combined organic extracts were washed with H₂O (2×3 L), dried (Na₂SO₄) and concentrated under reduced pressure to afford the title compound (144.0 g, 52.3% of total possible (S)-enantiomer).

Chiral HPLC assays were determined on samples of (S)-N-[6-benzyloxy-2,3-dihydrobenzofuran-3-yl] hydroxylamine-(S)-mandelate which were converted to free hydroxylamine by dissolving the salt in EtOAc and adding H₂O and excess aqueous NH₄OH. The assay system consisted of a Chiralpak AD column (4.6 mm×25 cm), which was eluted with 10% isopropanol/hexane at a flow rate of 1 mL/min using a uv detector at 210 nm. A single peak was observed at 24.2 min.

EXAMPLE 5

(S)-N-[6-Benzyloxy-2,3-dihydrobenzofuran-3-yl] hydroxyurea

To a 5 L, 3-necked flask equipped with a mechanical stirrer, thermometer and condenser with CaCl₂ drying tube was added under a N₂ atmosphere (S)-N-[6-benzyloxy-2,3-dihydrobenzofuran-3-yl]hydroxylamine (129.0 g, 0.501 mol) in THF (2.6 L). The resulting mixture was stirred at room temperature for 0.5 h, at which time was added in one portion, trimethylsilylisocyanate (107.2 mL, 86.6 g, 0.752 mol). The mixture was then heated at reflux for 15 min, then was cooled to 5° C. with an ice bath. The precipitate which formed was collected by filtration to afford a white solid. A second crop of peach-colored solid was obtained from concentration of the filtrate. This was taken up in a minimum of DMF, heated and treated with Darco. Filtration and cooling afforded a white solid which was collected, dried and combined with the first crop. The combined solids were dissolved in EtOH (20 vol), heated to reflux, cooled, collected and dried to afford the title compound (105.4 g, 70.2%); m.p. 192.5°–193° C.

Analysis by reversed-phase HPLC (Zorbax RX C₈ column, 4.6 mm×15 cm; mobile phase of 0.1:50:50 TFA/MeOH/H2O) gave a single peak and chiral HPLC (Chiracel OJ, 4.6 mm×25 cm; mobile phase of 40:60 EtOH/hexane; flow rate 1.0 mL/min; uv detector at 210 nm) gave a single peak at 18.3 min.

EXAMPLE 6

(R,S)-N-(6-Benzyloxy-2,3-dihydrobenzofuran-3-yl)-hydroxyamine a) 6-Hydroxy-3-oxo-2,3-Dihydrobenzofuran To a stirred solution of resorcinol (16.0 kg, 145 moles), chloroacetonitrile (13.2 kg, 175 moles) and ethyl acetate (193 kg, 214 L)under nitrogen was added zinc chloride (11.0 kg, 80.8 moles) and the mixture cooled to 5° C. Hydrogen chloride gas (31.2 kg, 855 moles) was bubbled in at such a rate that the internal temperature did not exceed 30° C. The thick slurry was stirred for an additional 2 hours and the solvent removed by vacuum distillation. Water (80 L) was added and the residual ethyl acetate removed by vacuum distillation. The mixture was heated to 60° C. and stirred for 1 hour. The temperature was cooled to 20° C. and then t-butyl methyl ether (146 L, 113 kg) was added and the mixture stirred for 15 minutes. The aqueous layer was separated and the organic layer washed with water (50 L). The layers were separated and the organic layer removed by vacuum distillation. 95% Ethanol (50 L) was added and the distillation continued until all of the t-butyl methyl ether had been removed. Then 95% ethanol (220 L) was added followed by the addition of sodium acetate (21.8 kg, 266 moles) and the mixture heated to reflux for 1 hour. Additional sodium acetate (3.54 kg, 43.2 moles) was added and the mixture refluxed for an additional 1 hour. The mixture was cooled to 5° C. and the solid collected by centrifugation. This was washed with 95% ethanol (51 L), water (800 L), 95% ethanol (29 L) and hexane (30 L). The material was dried at 40° C. under vacuum to afford the desired product (16.5 kg, 75%) which was used without any further purification.

b) 6-Benzyloxy-2,3-dihydro-3-oxo-benzofuran

To a stirred solution of 6-hydroxy-3-oxo-2,3-dihydrobenzofuran of Example 6(a) (32 kg, 213 moles) in DMF (192 L) was added potassium carbonate (31.0 kg, 224 moles). After stirring for 5 min. at room temperature, benzyl bromide (145.2 kg, 264 moles) was added and the resulting mixture was stirred for 2 hours at room temperature. The mixture was poured into water (651 L), stirred for 30 minutes and the product collected by centrifugation. The crude solid was washed with water (580 L), 80% ethanol (100 L) and dried under vacuum to afford the desired product (49.1 kg; 95%) which was used without any further purification.

c) 6-Benzyloxy-2,3-Dihydrobenzofuran-3-oxime

A stirred mixture of 6-benzyloxy-2,3-dihydro-3-oxo-benzofuran of Example 6(b) above (24 kg, 99.9 moles), hydroxylamine hydrochloride (15.0 kg, 216 moles), sodium acetate (24.6 kg, 300 moles) and ethanol (216 L) was heated at reflux for 2 hours. The mixture was poured into water (534 L) and the vessel was rinsed with 95% ethanol (20 L) and this added to the water mixture and stirred for 1 hour. The solid was collected by centrifugation, washed with water (670 L), 95% ethanol (80 L), and dried at 55° C. under vacuum to afford the desired product as an orange solid (24.3 kg, 95%) which was used without any further purification.

d) (R,S)-N-(6-Benzyloxy-2,3-dihydrobenzofuran-3-yl)-hydroxylamine

To a stirred mixture of 6-benzyloxy-2,3-dihydrobenzofuran-3-oxime of Example 6(c) above, (16.0 kg, 62.7 moles) in methanol (200 L) and dichloromethane (200 L) cooled to 5° C. was added pyridine-borane complex (32.1 kg, 345 moles). A solution of 6N HCl (60.0 L, 360 moles) was added at such a rate that the internal temperature did not exceed 10° C. and the resulting solution was stirred for 18 hours at ambient temperature. The solvents were removed under reduced pressure and then tert-butyl methyl ether (50 kg) was added followed by 3N HCl (64 L, 192 moles). The reaction mixture was stirred for 2 hours at room temperature and the crude solid collected by centrifugation and washed with water (50 L). The wet cake was suspended in water (192 L) and the pH adjusted to 6.5–7.0 with 50% NaOH (4.0 L). The mixture w28 as allowed to stir overnight at ambient temperature. The pH was adjusted to 9.5 with concentrated NH₄OH (2.8 kg), stirred for 30 min, the product collected by centrifugation, washed with water (230 L), 95% ethanol (80 L) and dried at 55° C. under vacuum to afford an off white solid (14.2 kg, 88%) which was used without further purification.

EXAMPLE 7

(S)-N-(6-Benzyloxy-2,3-dihydrobenzofuran-3-yl)-N-hydroxyurea (a) S)-N-(6-Benzyloxy-2,3-dihydrobenzofuran-3-yl) hydroxylamine, (S)-(+)-mandelic acid salt To a stirred refluxing suspension of (R,S)-N-(6-benzyloxy-2,3-dihydrobenzo-furan-3-yl)-hydroxylamine of Example 6(d), (14.0 kg, 54.4 moles) in methanol (460 L)

was added a solution of S-(+)-mandelic acid (8.29 kg, 54.5 moles) in methanol (30 L). The resulting clear solution was refluxed for 30 min and allowed to cool, with stirring, to 38°–40° C. over a 1.5 hour period. When the reaction mixture had cooled to 39° C., it was seeded with S)-N-(6-benzyloxy-2,3-dihydrobenzofuran-3-yl)hydroxylamine, (S)-(+)-mandelic acid salt (4 g) and the temperature was held at 34°–36° C for 30 min. The suspension was then cooled to 20°–25° C. over 1 hour and stirred for 4 hours at this temperature. The solid collected by centrifugation, washed with ethyl acetate (35 L) and dried under vacuum at 45°–50° C. to afford a white solid (7.70 kg, 34%) which was used without further purification. Chiral HPLC analysis showed an optical purity of 99.4% of the desired (S)-enantiomer.

b) (S)-N-(6-Benzyloxy-2,3-dihydrobenzofuran-3-yl) hydroxylamine

To a stirred suspension of (S)-N-(6-benzyloxy-2,3-dihydrobenzofuran-3-yl)hydroxylamine, (S)-(+)-mandelic acid salt of Example 7(a) above, (18.0 kg, 44.0 moles) in water (174 L) and ethyl acetate (465 L) was added concentrated $NH_4OH$ (ca. 4.4 L) until a pH of ca. 9.5 was achieved. The solution was stirred for 15 min. and the layers separated. The aqueous layer was washed with ethyl acetate (2×100 L) and the organic layers were combined and washed with water (3×175 L). The layers were separated and the ethyl acetate was distilled under reduced pressure until a solid started to appear. Hexane (300 L) was added and the temperature lowered to 5° C. and stirred for 1 hour. The product was collected by centrifugation, washed with hexane (90 L) and dried under vacuum to afford a white solid (10.2 kg, 90%) which was used without any further purification. The product was greater than 99% e.e. as determined by chiral HPLC.

c) (S)-N-(6-Benzyloxy-2,3-dihydrobenzofuran-3-yl)-N-hydroxyurea

To a stirred solution of (S)-N-(6-benzyloxy-2,3-dihydrobenzofuran-3-yl)hydroxyamine of Example 7(b) above, (10.0 kg, 38.9 moles), DMF (50.0 L), and acetic acid (3.34 L) cooled to 5° C. was added in one portion, a cooled (0° C.) solution of potassium cyanate (4.73 kg, 58.3 moles) in water (9.0 L). This was added at such a rate that the internal temperature did not exceed 10° C. The resultant suspension was stirred for 30 min at room temperature. Water (213 L) was added and the mixture stirred for 1 hour at ambient temperature. The product was collected by centrifugation and the wet cake washed with water (425 L) and 95% ethanol (40 L). The product was isolated an dried at 45°–50° C. under vacuum to afford the crude product (11.4, 97%) as an off white solid. The crude product (11.0 kg) was recrystallized from DMF/TBME (110 L/233 L)) and washed with TBME (89 L) to afford the desired compound (9.1 kg, 83%) as a white solid after drying at 45°–50° C. under vacuum. The product was greater than 99% e.e. as determined by chiral HPLC.

EXAMPLE 8

(R,S)-N-[6-(2,6-Diflurobenzyloxy)-2,3-dihydrobenzofuranyl]-N-hydroxylamine a) 6-(2,6-Diflurobenzyloxy)-3-oxo-2,3-dihydrobenzofuran To a stirred solution of 6-hydroxy-3-oxo-2,3-dihydrobenzofuran (100 g, 0.67 moles) in DMF (600 mL) was added potassium carbonate (185 g, 1.3 moles). After stirring for 5 min. at room temperature, a solution of a-bromo-2,6-difluorotoluene (171.8 g, 0.83 moles) in DMF (100 mL) was added and the resulting mixture was stirred for 3 hours at room temperature. The mixture was poured into water (2.5 L), stirred for 30 minutes and the product collected by filtration. The crude solid was washed with water (4 L), absolute ethanol (500 mL) and dried under vacuum to afford the desired product (185 g, 99%) which was used without any further purification. Mp 134°–138° C.; 300 MHz $^1$H NMR ($CDCl_3$): d 4.61 (s, 2H); 5.17 (s, 2H); 6.67–6.70 (m, 2H); 6.91–6.99 (m, 2H); 7.31–7.41 (m, 1H); 7.56 (d, 1H).

b) 6-(2,6-Diflurobenzyloxy)-3-oximino-2,3-dihydrobenzofuran

A stirred mixture of 6-(2,6-difluorobenzyloxo)-3-oxo-2,3-dihydrobenzofuran (185 g, 0.67 moles), hydroxylamine hydrochloride (95.9 g, 1.38 moles), sodium acetate (109.9 g, 1.34 moles) and ethanol (1.4 L) was heated at reflux for 3 hours. The mixture was poured into water (2.4 L) and the flask rinsed with water (1 L). The orange solid was collected by filtration, washed with hexane (2 L) and dried at 55° C. under vacuum to afford the desired product as an orange solid (188.4 g, 96%) which was used without any further purification. Mp 166°–172° C.; 300 MHz $^1$H NMR ($CDCl_3$): (mixture of syn and anti isomers) d 5.02 (s, 0.5H); 5.12 (s, 2H); 5.20 (s, 1.5H); 6.50–6.68 (m, 2H); 6.89–7.00 (m, 2H); 7.28–7.41 (m, 1H); 7.48 (d, 0.75H); 7.50–7.70 (br s, 1H); 8.17 (d, 0.25H).

c) (R,S)-N-[6-(2,6-Diflurobenzyloxy)-2,3-dihydrobenzofuranyl]-N-hydroxylamine

To a stirred mixture of 6-(2,6-difluorobenzyloxy)-3-oximino-2,3-dihydrobenzofuran (161.0 g, 0.55 moles) in methanol (1.8 L) and dichloromethane (1.8 L) cooled to 5° C. was added pyridine-borane complex (286 g, 3.1 moles). A solution of 6N HCl (540 mL) was added at such a rate that the internal temperature did not exceed 10° C. and the resulting solution was stirred for 18 hours at ambient temperature. The solvents were removed under reduced pressure and then tert-butyl methyl ether (560 mL) was added followed by 3N HCl (560 mL). The reaction mixture was stirred for 2 hours at room temperature and the crude solid collected by filtration and washed with water (500 mL). The wet cake was suspended in water (310 mL) and the pH adjusted to 6.5 with 50% NaOH (40 mL). The mixture was allowed to stir overnight at ambient temperature. The pH was adjusted to 9.5 with concentrated $NH_4OH$, stirred for 1 hour, the product collected by filtration, washed with water (500 mL) and dried at 55° C. under vacuum to afford an off white solid (146.2 g, 90%) which was used without further purification. Mp 146°–150° C.; 300 MHz $^1$H NMR (DMSO-$d_6$): d 4.44–4.46 (m, 2H); 4.49–4.54 (m, 1H); 5.04 (s, 2H); 6.04 (br s, 1H); 6.46–6.49 (m, 2H); 7.11–7.19 (m, 2H); 7.24 (d, 1H); 7.45–7.53 (m, 2H).

EXAMPLE 9

(S)-(+)-N-3-[6-(2,6-Diflourobenzyloxy)-2,3-Dihydrobenzofuranyl]-N-hydroxyurea a) (S)-N-[6-(2,6-Difluorobenzyloxy)-2,3-dihydrobenzofuranyl]-hydroxylamine, (S)-(+)-mandelic acid salt A stirred suspension of (R,S)-N-[6-(2,6-difluorobenzyloxy)-2,3-dihydrobenzo-furanyl]-N-hydroxylamine of Example 6 above (93.7 g, 0.32 moles) and S-(+)-mandelic acid (48.8 g, 0.32 moles) in ethyl acetate (1.87 L) was heated to reflux to afford a nearly clear solution. The solution was filtered through a Buchner funnel (to remove particulate matter) and allowed to cool, with stirring, to room temperature over a one hour period which caused crystallization. The suspension was stirred at ambient temperature for 2 hours, the solid collected by filtration, washed with ethyl acetate (100 mL) and dried under vacuum at 40° C. to afford 50.6 g of a whim solid. Chiral HPLC indicated a 5:1 diastereomeric ratio. Several lots of crude (S)-N-[6-(2,6-difluorobenzyloxy)-2,3-dihydrobenzofuranyl]-hydroxylamine, (S)-(+)-mandelic acid salt (60.9 g, 0.137 moles) was suspended in ethyl acetate (1.85 L), heated to reflux, filtered and the filtrate allowed to slowly cool, with stirring, to ambient temperature. The mixture was then cooled and stirred at 15° C. for one hour. The product was collected by filtration, washed with ethyl acetate and dried under vacuum to afford 41.4 g of a white solid. The product was greater than 99% e.e. as determined by chiral HPLC. Mp 140°–145° C.; $[\alpha]_D$=+161.57° (c 1.08, MeOH,); 300 MHz $^1$H NMR (DMSO-$d_6$): d 4.44–4.46 (m, 2H); 4.47–4.54 (m, 1H); 5.00 (s, 1H); 5.04 (s, 2H); 6.46–6.49 (m, 2H); 7.11–7.19 (m, 2H); 7.23–7.42 (complex m, 6H); 7.45–7.55 (m, 2H).

b) (S)-N-[6-(2,6-Difluorobenzyloxy)-2,3-Dihydrobenzofuranyl]-hydroxylamine

To a stirred suspension of (S)-N-[6-(2,6-difluorobenzyloxy)-2,3-dihydrobenzo-furanyl]-hydroxylamine, (S)-(+)-mandelic acid salt of part Example 9(a) (45.4 g, 0.10 moles) in water (425 mL) and ethyl acetate (1.0 L) was added concentrated NH$_4$OH (ca. 15 mL) until a pH of ca. 9.5 was achieved. The solution was stirred for 15 min. and the layers separated. The aqueous layer was washed with ethyl acetate (2×210 mL) and the organic layers were combined and washed with water (2×425 mL). The layers were separated and the ethyl acetate was distilled under reduced pressure until a solid started to appear. Hexane (850 mL) was added and the temperature lowered to 5° C. and stirred for 1 hour. The product was collected by filtration, washed with hexane and dried under vacuum to afford a white solid (27.7 g, 93%) which was used without any further purification. The product was greater than 99% e.e. as determined by chiral HPLC. Mp 118°–120° C.; $[\alpha]_D$=+20.89° (c 1.45, MeOH); 300 MHz $^1$H NMR (DMSO-$d_6$): d 4.44–4.46 (m, 2H); 4.47–4.51 (m, 1H); 5.04 (s, 2H); 5.91 (s, 1H); 6.46–6.49 (m, 2H); 7.11–7.20 (m, 2H); 7.24 (d, 1H); 7.45–7.55 (m, 2H).

c) (S)-(+)-N-3-[6-(2,6-Difluorobenzyloxy)-2,3-Dihydrobenzofuranyl]-N-hydroxyurea To a stirred solution of (S)-(+)-N-3-[6-(2,6-difluorobenzyloxy)-2,3-dihydrobenzofuranyl]-N-hydroxylamine of Example 7(b) above (27.7 g, 0.094 moles), DMF (123 mL), and acetic acid (8.2 mL) cooled to 5° C. was added in one portion, a solution of potassium cyanate (11.6 g, 0.143 moles) in water (21 mL). The resultant suspension was stirred for 30 min at room temperature. Water (480 mL) was added and the mixture stirred for 1 hour at ambient temperature. The product was collected by filtration and the wet cake slurried in water (500 mL). The product was isolated an dried at 50° C. under vacuum to afford the crude product (29.5 g, 92%) as an off white solid. The material was recrystallized from DMF/TBME/H$_2$O (150 mL/500 mL/500 mL) followed by a hexane (500 mL) slurry to afford the desired compound (25.6 g, 80%) as a white solid drier drying. The product was greater than 99% e.e. as determined by chiral HPLC.; $[\alpha]_D$=+77.79° (c 1.18, MeOH); 300 MHz $^1$H NMR (DMSO-$d_6$): d 4.43–4.48 (m, 1H); 4.56 (t, 1H); 5.04 (s, 2H); 5.76–5.81 (m, 1H); 6.48–6.51 (m, 4H); 7.07 (d, 1H); 7.12–7.20 (m, 2H); 7.46–7.56 (m, 1H); 9.12 (s, 1H ); mass spectrum CI/CH$_4$ m/e 337 (M+H)$^+$. Anal. Calcd for C$_{16}$H$_{14}$F$_2$N$_2$O$_4$: C, 57.15; H, 4.20; F, 11.30; N, 8.33. Found: C, 57.33; H, 4.12; F, 10.98; N, 8.27.

EXAMPLE 10

R,S)-N-(6-Benzyloxy-2,3-dihydrobenzyfuran-3-yl)-hydroxylamine a) 6-Hydroxy-3-oxo-2,3-Dihydrobenzofuran To a stirred solution of resorcinol (16.0 kg, 145 moles), chloroacetonitrile (13.2 kg, 175 moles) and ethyl acetate (193 kg, 214 L)under nitrogen was added zinc chloride (11.0 kg, 80.8 moles) and the mixture cooled to 5° C. Hydrogen chloride gas (31.2 kg, 855 moles) was bubbled in at such a rate that the internal temperature did not exceed 30° C. The thick slurry was stirred for an additional 2 hours and the solvent removed by vacuum distillation. Water (80 L) was added and the residual ethyl acetate removed by vacuum distillation. The mixture was heated to 60° C. and stirred for 1 hour. The temperature was cooled to 20° C. and then t-butyl methyl ether (146 L, 113 kg) was added and the mixture stirred for 15 minutes. The aqueous layer was separated and the organic layer washed with water (50 L). The layers were separated and the organic layer removed by vacuum distillation. 95% Ethanol (50 L) was added and the distillation continued until all of the t-butyl methyl ether had been removed. Then 95% ethanol (220 L) was added followed by the addition of sodium acetate (21.8 kg, 266 moles) and the mixture heated to reflux for 1 hour. Additional sodium acetate (3.54 kg, 43.2 moles) was added and the mixture refluxed for an additional 1 hour. The mixture was cooled to 5° C. and the solid collected by centrifugation. This was washed with 95% ethanol (51 L), water (800 L), 95% ethanol (29 L) and hexane (30 L). The material was dried at 40° C. under vacuum to afford the desired product (16.5 kg, 75%) which was used without any further purification.

b) 6-Benzyloxy-2,3-dihydro-3-oxo-benzofuran

To a stirred solution of 6-hydroxy-3-oxo-2,3-dihydrobenzofuran of Example 10(a) (32 kg, 213 moles) in DMF (192 L) was added potassium carbonate (31.0 kg, 224 moles). After stirring for 5 min. at room temperature, benzyl bromide (45.2 kg, 264 moles) was added and the resulting mixture was stirred for 2 hours at room temperature. The mixture was poured into water (651 L), stirred for 30 minutes and the product collected by centrifugation. The crude solid was washed with water (580 L), 80% ethanol (100 L) and dried under vacuum to afford the desired product (49.1 kg, 95%) which was used without any further purification.

c) 6-Benzyloxy-2,3-Dihydrobenzofuran-3-oxime

A stirred mixture of 6-benzyloxy-2,3-dihydro-3-oxo-benzofuran of Example 10(b) above (24 kg, 99.9 moles), hydroxylamine hydrochloride (15.0 kg, 216 moles), sodium acetate (24.6 kg, 300 moles) and ethanol (216 L) was heated at reflux for 2 hours. The mixture was poured into water (534 L) and the vessel was rinsed with 95% ethanol (20 L) and this added to the water mixture and stirred for 1 hour. The solid was collected by centrifugation, washed with water (670 L), 95% ethanol (80 L), and dried at 55° C. under vacuum to afford the desired product as an orange solid (24.3 kg, 95%) which was used without any further purification.

d) (R,S)-N-(6-Benzyloxy-2,3-dihydrobenzofuran-3-yl)-hydroxylamine

To a stirred mixture of 6-benzyloxy-2,3-dihydrobenzofuran-3-oxime Example 10(c) above, (16.0 kg, 62.7 moles) in methanol (200 L) and dichloromethane (200 L) cooled to 5° C. was added pyridine-borane complex (32.1 kg, 345 moles). A solution of 6N HCl (60.0 L, 360 moles) was added at such a rate that the internal temperature did not exceed 10° C. and the resulting solution was stirred for 18 hours at ambient temperature. The solvents were removed under reduced pressure and then tert-butyl methyl ether (50 kg) was added followed by 3N HCl (64 L, 192 moles). The reaction mixture was stirred for 2 hours at room temperature and the crude solid collected by centrifugation and washed with water (50 L). The wet cake was suspended in water (192 L) and the pH adjusted to 6.5–7.0 with 50% NaOH (4.0 L). The mixture was allowed to stir overnight at ambient temperature. The pH was adjusted to 9.5 with concentrated NH₄OH (2.8 kg), stirred for 30 min, the product collected by centrifugation, washed with water (230 L), 95% ethanol (80 L) and dried at 55° C. under vacuum to afford an off white solid (14.2 kg, 88%) which was used without further purification.

EXAMPLE 11

(S)-N-(6-Benzyloxy-2,3-dihydrobenzofuran-3-yl)-N-hydroxyurea (a) S-N-(6-Benzyloxy-2,3-dihydrobenzofuran-3-yl) hydroxylamine, (S)-(+)-mandelic acid salt To a stirred refluxing suspension of (R,S)-N-(6-benzyloxy-2,3-dihydrobenzo-furan-3-yl)-hydroxylamine (14.0 kg, 54.4 moles) in methanol (460 L) was added a solution of S-(+)-mandelic acid (8.29 kg, 54.5 moles) in methanol (30 L). The resulting clear solution was refluxed for 30 min and allowed to cool, with stirring, to 38°–40° C. over a 1.5 hour period. When the reaction mixture had cooled to 39° C., it was seeded with S)-N-(6-Benzyloxy-2, 3-dihydrobenzofuran-3-yl)hydroxylamine, (S)-(+)-mandelic acid salt (4 g) and the temperature was held at 34°–36° C. for 30 min. The suspension was then cooled to 20°–25° C. over 1 hour and stirred for 4 hours at this temperature. The solid collected by centrifugation, washed with ethyl acetate (35 L) and dried under vacuum at 45°–50° C. to afford a white solid (7.70 kg, 34%) which was used without further purification. Chiral HPLC showed an optical purity of 99.4% of the desired (S)-enantiomer.

b) (S)-N-(6-Benzyloxy-2,3-dihydrobenzofuran-3-yl) hydroxylamine

To a stirred suspension of (S)-N-(6-benzyloxy-2,3-dihydrobenzofuran-3-yl)hydroxylamine, (S)-(+)-mandelic acid salt, (18.0 kg, 44.0 moles) in water (174 L) and ethyl acetate (465 L) was added concentrated NH₄OH (ca. 4.4 L) until a pH of ca. 9.5 was achieved. The solution was stirred for 15 min. and the layers separated. The aqueous layer was washed with ethyl acetate (2×100 L) and the organic layers were combined and washed with water (3×175 L). The layers were separated and the ethyl acetate was distilled under reduced pressure until a solid started to appear. Hexane (300 L) was added and the temperature lowered to 5° C. and stirred for 1 hour. The product was collected by centrifugation, washed with hexane (90 L) and dried under vacuum to afford a white solid (10.2 kg, 90%) which was used without any further purification. The product was greater than 99% e.e. as determined by chiral HPLC.

c) (S)-N-(6-Benzyloxy-2,3-dihydrobenzofuran-3-yl)-N-hydroxyurea

To a stirred solution of (S)-N-(6-benzyloxy-2,3-dihydrobenzofuran-3-yl)hydroxylamine (10.0 kg, 38.9 moles), DMF (50.0 L), and acetic acid (3.34 L) cooled to 5° C. was added in one portion, a cooled (0° C.) solution of potassium cyanate (4.73 kg, 58.3 moles) in water (9.0 L). This was added at such a rate that the internal temperature did not exceed 10° C. The resultant suspension was stirred for 30 min at room temperature. Water (213 L) was added and the mixture stirred for 1 hour at ambient temperature. The product was collected by centrifugation and the wet cake washed with water (425 L) and 95% ethanol (40 L). The product was isolated an dried at 45°–50° C. under vacuum to afford the crude product (11.4, 97%) as an off white solid. The crude product (11.0 kg) was recrystallized from DMF/TBME (110 L/233 L) and washed with TBME (89 L) to afford the desired compound (9.1 kg, 83%) as a white solid after drying at 45°–50° C. under vacuum. The product was greater than 99% e.e. as determined by chiral HPLC.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A process for resolving a mixture of enantiomeric hydroxylamines of formula (I)

[R*NHOZ]   (I)

in which [R*NHOZ] is a mixture of enantiomeric hydroxylamines wherein
R* is an organic radical which contains a chiral carbon to which the hydroxylamine group is attached; and
Z is hydrogen or a hydroxyl protecting group;
which process comprises
a) treating a mixture of enantiomers of the formula R*NHOZ with a homochiral organic acid [HA*] to form a mixture of diasteriomeric acid addition salts of the formula

[R*NH₂OZ]⁺[A*]⁻   (II); and

b) separating the desired diasteriomeric acid addition salt.

2. The process according to claim 1 wherein the organic radical (R*) is selected from:
a) compounds of the formula (IA)

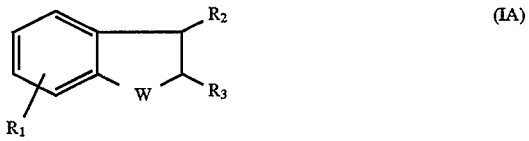

in which one of R₂ and R₃ is hydrogen; and the other is the chiral carbon (C*) to which the hydroxylamine group NHOZ is attached;
W is $CH_2(CH_2)_s$, $O(CH_2)_s$, $S(CH_2)_s$, or $NR_4(CH_2)_s$;
R₄ is hydrogen, $(C_{1-4})$alkyl, phenyl, $(C_{1-6})$alkanoyl or aroyl;
s is a number having a value of 0 to 3, provided that when R₂ is hydrogen and W is $O(CH_2)_s$ or $S(CH_2)_s$, then s is 1 to 3 and when W is $NR_4(CH_2)_s$ then s is 1 to 3 and R₃ is hydrogen;
R₁ is selected from the group consisting of hydrogen, $(C_{1-10})$alkyl, $(C_{1-10})$alkoxy, naphthyl, $(CH_2)_m$—Ar—$(X)_v$, $(CH_2)_m(C=C)_n(CH_2)_p$—Ar—$(X)_v$, $O(CH_2)_m$Ar—$(X)_v$, $S(CH_2)_m$—Ar—$(X)_v$, or $N(CH_2)_m$—Ar—$(X)_v$;

p is 0 or an integer having a value of 1, 2, or 3;
m is 0 or an integer having a value of 1, 2, or 3;
n is 0 or an integer having a value of 1, 2, or 3;
v is 0 or an integer having a value of 1, 2, or 3;
Ar is selected from the group consisting of phenyl, naphthyl, quinolyl, isoquinolyl, pyridyl, furanyl, imidazoyl, benzimidazoyl, triazolyl, oxazolyl, isoxazolyl, thiazole, or thienyl;
X is a member selected from the group consisting of hydrogen, halogen, ($C_{1-10}$)alkyl, ($C_{5-8}$)cycloalkyl, ($C_{2-10}$)alkenyl, hydroxy, carboxy(CHY)$_r$, ($C_{1-10}$) alkoxy, ($C_{1-10}$)alkylthio, ($C_{1-10}$)alkylsulphinyl, ($C_{1-10}$)alkylsulphonyl, aryloxy, aryl($C_{1-6}$)alkyloxy, halo ($C_{1-6}$)alkyl, hydroxy($C_{1-6}$)alkyl, ($R_5$)$_2$N(CHY)$_r$, or cyano; provided that if v is a number greater then 1 then one substituent must be selected from alkyl, ($C_{1-10}$)alkoxy or halo; t is 0 or 1;
$R_5$ is hydrogen or ($C_{1-6}$)alkyl;
Y is hydrogen or ($C_{1-3}$)alkyl;
t' is 0 or 1; and if t' is 1 than one of $R_5$ must be hydrogen; or a salt thereof; or b) compounds of formula (IB):

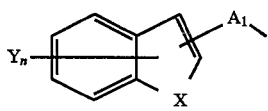

wherein $A_1$ contains the C* (chiral carbon adjacent to the hydroxylamine group NHOZ attachment);
$A_1$ may be a $C_{1-6}$ alkylene or $C_{2-6}$ alkenylene group;
Y is selected independently at each occurrence from hydrogen, halogen, hydroxy, cyano, halosubstituted alkyl, $C_{1-12}$ alkyl, $C_{2-12}$ alkenyl, $C_{1-12}$ alkoxy, $C_{3-8}$ cycloalkyl, $C_{1-12}$ thioalkyl, aryl, aryloxy, aroyl, $C_{1-12}$ arylalkyl, $C_{1-12}$ arylalkenyl, $C_{1-12}$ arylalkoxy, $C_{1-12}$ arylthioalkoxy and substituted derivatives of aryl, aryloxy, aroyl, $C_{1-12}$ arylalkyl, $C_{2-12}$ arylalkenyl, $C_{1-12}$ arylalkoxy, $C_{1-12}$ arylthioalkoxy wherein substituents are selected from halo, nitro, cyano, $C_{1-12}$ alkyl, alkoxy, and halosubstituted alkyl; and
n is 1 to 5;
X is oxygen, sulfur, S(O)$_2$ or NR$_1$;
$R_1$ is hydrogen, $C_{1-6}$ alkyl, $C_{1-6}$ alkanoyl, aroyl, or alkylsulfonyl;
the dotted line within the five membered ring signifies a single or double bond;
or a salt thereof; or c) compounds of formula (IC):

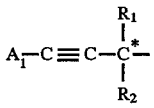

wherein:
$A_1$ is $C_{5-20}$ alkyl, cycloalkyl, aryl, aryloxy, arylcycloalkyl, aryloxy alkyl, arylalkoxyalkyl, arylthioalkyl, Aryl NH-alkyl, N-Aryl-N-(alkylkamino alkyl, N-(Aryl-alkylamino alkyl), N-(Aryl-alkyl)-N-(alkyl amino)alkyl, optionally substitued 2- or 3-furyl, optionally substitued 2- or 3-thienyl, optionally substitued benzo(b)furyl, or optionally substituted benzo(b)thienyl;
wherein C* denotes the chiral carbon adjacent to which the NHOZ moiety is attached;
$R_1$ and $R_2$ are independently hydrogen, $C_{1-6}$ alkyl, aryl, heteroaryl, heteroaryl alkyl, heterocyclyl, heterocyclyl alkyl or $C_{3-8}$ cycloalkyl, provided that $R_1$ and $R_2$ are not both the same.

3. The process according to claim 1 wherein the homochiral organic acid HA* is mandelic acid.
4. The process according to claim 1 wherein separation of the desired diasteriomeric acid salt is by disolution into a suitable solvent and crystallization thereof.
5. The process according to claim 4 wherein the suitable solvent is selected from ethyl acetate or an alcohol, or a mixture thereof.
6. The process according to claim 5 wherein the alcohol is methanol or ethanol.
7. The process according to claim 1 wherein the separation is by fractional crystallisation.
8. The process according to claim 1 wherein the diasteriomeric acid addition salt is composed of a homochiral organic acid HA* which is either the (+)- or (−)-enantiomer.
9. The process according to claim 8 wherein the diasteriomeric acid addition salt is composed of a homochiral hydroxylamine [R*NHOZ] which is either the (+)- or (−)-enantiomer.
10. The process according to claim 9 wherein the [R*NHOZ][HA*] salt is selected from the combinations of (+)(+), (+)(−), (−)(+) or (−)(−) entantiomers.
11. The process according to claim 10 wherein the R* is selected from Formula (IA) wherein R$_3$ is hydrogen, W is O(CH$_2$)$_s$, and s is 0; or R* is Formula (IC), and one of R$_1$ and R$_2$ is hydrogen and the other is methyl, and A$_1$ is an optionally substituted 2-furanyl.
12. The process according to claim 1 wherein the diasteriomeric acid addition salt is
(S)-N-(6-benzyloxy-2,3-dihydrobenzofuran-3-yl) hydroxylamine (S)-mandelate;
(R)-N-(6-benzyloxy-2,3-dihydrobenzofuran-3-yl) hydroxylamine (S)-mandelate;
(S)-N-(6-[2,6-difluoro-benzyloxy]-2,3-dihydrobenzofuran-3-yl)hydroxylamine (S)-mandelate;
(R)-N-(6-[2,6-difluro-benzyloxy]-2,3-dihydrobenzofuran-3-yl)hydroxylamine (S)-mandelate;
(S)-N-(1-benzo[b]thien-2-yl-ethyl)hydroxylamine (S)-mandelate;
(R)-N-(1-benzo[a]thien-2-yl-ethyl)hydroxylamine (S)-mandelate;
(S)-N-(1-benzo[b]thien-2-yl-ethyl)hydroxylamine (R)-mandelate;
(R)-N-(1-benzo[b]thien-2-yl-ethyl)hydroxylamine (R)-mandelate;
(S)-N-(4-[5-(4-Fluorophenoxy)-2-furyl]-3-butyn-2-yl] hydroxylamine (S)-mandelate;
(R)-N-(4-[5-(4-Fluorophenoxy)-2-furyl]-3-butyn-2-yl] hydroxylamine (S)-mandelate;
(S)-N-(4-[5-(4-Fluorophenoxy)-2-furyl]-3-butyn-2-yl] hydroxylamine (R)-mandelate; or
(R)-N-(4-[5-(4-Fluorophenoxy)-2-furyl]-3-butyn-2-yl] hydroxylamine (R)-mandelate.
13. A process for preparing a diastereoisomeric acid addition salt of formula (II)

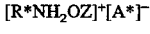

in which [R*NHOZ]$^+$ is a homochiral hydroxylamine; R* is a homochiral organic moiety which contain a chiral carbon to which the NHOZ group is attached, and Z is hydrogen or a hydroxyl protecting group; and HA* is a homochiral organic acid; which process comprises treating the corresponding racemic or partially resolved hydroxylamine [R*NHOZ] with the homochiral organic acid HA* in a suitable solvent, to form a pair of diastereoisomeric acid addition salts.
14. The process according to claim 13 wherein the racemic or partially resolved hydroxylamine [R*NHOZ] containing the organic radical (R*) is selected from:

a) compounds of the formula (IA) wherein R* is:

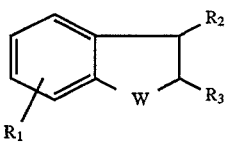

in which one of $R_2$ and $R_3$ is hydrogen; and the other is the chiral carbon (C*) to which the hydroxylamine group NHOZ is attached;
W is $CH_2(CH_2)_s$, $O(CH_2)_s$, $S(CH_2)_s$, or $NR_4(CH_2)_s$;
$R_4$ is hydrogen, $(C_{1-4})$alkyl, phenyl, $(C_{1-6})$alkanoyl or aroyl;
s is a number having a value of 0 to 3, provided that when $R_2$ is hydrogen and W is $O(CH_2)_s$ or $S(CH_2)_s$, then s is 1 to 3 and when W is $NR_4(CH_2)_s$ then s is 1 to 3 and $R_3$ is hydrogen;
$R_1$ is selected from the group consisting of hydrogen, $(C_{1-10})$alkyl, $(C_{1-10})$alkoxy, naphthyl, $(CH_2)_m$—Ar—$(X)_v$, $(CH_2)_m(C{=}C)_n(CH_2)_p$—Ar—$(X)_v$, $O(CH_2)_m$Ar—$(X)_v$, $S(CH_2)_m$—Ar—$(X)_v$, or $N(CH_2)_m$—Ar—$(X)_v$;
p is 0 or an integer having a value of 1, 2, or 3;
m is 0 or an integer having a value of 1, 2, or 3;
n is 0 or an integer having a value of 1, 2, or 3;
v is 0 or an integer having a value of 1, 2, or 3;
Ar is selected from the group consisting of phenyl, naphthyl, quinolyl, isoquinolyl, pyridyl, furanyl, imidazoyl, benzimidazoyl, triazolyl, oxazolyl, isoxazolyl, thiazole, or thienyl;
X is a member selected from the group consisting of hydrogen, halogen, $(C_{1-10})$alkyl, $(C_{5-8})$cycloalkyl, $(C_{2-10})$alkenyl, hydroxy, carboxy$(CHY)_r$, $(C_{1-10})$ alkoxy, $(C_{1-10})$alkylthio, $(C_{1-10})$alkylsulphinyl, $(C_{1-10})$alkylsulphonyl, aryloxy, aryl$(C_{1-6})$alkyloxy, halo $(C_{1-6})$alkyl, hydroxy$(C_{1-6})$alkyl, $(R_5)_2N(CHY)_r$, or cyano; provided that if v is a number greater then 1 then one substituent must be selected from alkyl, $(C_{1-10})$alkoxy or halo;
$R_5$ is hydrogen or $(C_{1-6})$alkyl;
Y is hydrogen or $(C_{1-3})$alkyl;
t is 0 or 1; or a pharmaceutically acceptable salt, thereof; or b) compounds of formula (IB):

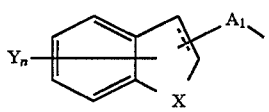

wherein $A_1$ is contains the C* (chiral carbon adjacent to the hydroxylamine group NHOZ attachment);
$A_1$ may be a $C_{1-6}$ alkylene or $C_{2-6}$ alkenylene group;
Y is selected independently at each occurrence from hydrogen, halogen, hydroxy, cyano, halosubstituted alkyl, $C_{1-12}$ alkyl, $C_{2-12}$ alkenyl, $C_{1-12}$ alkoxy, $C_{3-8}$ cycloalkyl, $C_{1-12}$ thioalkyl, aryl, aryloxy, aroyl, $C_{1-12}$ arylalkyl, $C_{1-12}$ arylalkenyl, $C_{1-12}$ arylalkoxy, $C_{1-12}$ arylthioalkoxy and substituted derivatives of aryl, aryloxy, aroyl, $C_{1-12}$ arylalkyl, $C_{2-12}$ arylalkenyl, $C_{1-12}$ arylalkoxy, $C_{1-12}$ arylthioalkoxy wherein substituents are selected from halo, nitro, cyano, $C_{1-12}$ alkyl, alkoxy, and halosubstituted alkyl;
the dotted line within the five membered ring signifies a single or double bond;
n is 1 to 5;
X is oxygen, sulfur, $S(O)_2$ or $NR_1$;
$R_1$ is hydrogen, $C_{1-6}$ alkyl, $C_{1-6}$ alkanoyl, aroyl, or alkylsulfonyl;

or a pharmaceutically acceptable salt thereof; or
c) compounds of formula (IC):

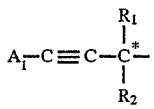

wherein:
$A_1$ is $C_{5-20}$ alkyl, cycloalkyl, aryl, aryloxy, arylcycloalkyl, aryloxy alkyl, arylalkoxyalkyl, arylthioalkyl, Aryl NH-alkyl, N-Aryl-N-(alkylkamino alkyl, N-(Aryl-alkylamino alkyl), N-(Aryl-alkyl)-N-(alkyl amino)alkyl, optionally substituted 2- or 3-furyl, optionally substitued 2- or 3-thienyl, optionally substitued benzo(b)furyl, or optionally substitued benzo(b)thienyl; wherein C* denotes the chiral carbon adjacent to which the NHOZ moiety is attached;
$R_1$ and $R_2$ are independently hydrogen, $C_{1-6}$ alkyl, aryl, heteroaryl, heteroaryl alkyl, heterocyclyl, heterocyclyl alkyl or $C_{3-8}$ cycloalkyl, provided that $R_1$ and $R_2$ are not both the same.

15. The process according to claim 13 wherein the homochiral organic acid HA* is mandelic acid.

16. The process according to claim 13 wherein the diasteriomeric acid addition salt is composed of a homochiral organic acid HA* which is either the (+)- or (−)-enantiomer.

17. The process according to claim 16 wherein the diasteriomeric acid addition salt is composed of a homochiral hydroxylamine [R*NHOZ] which is either the (+)- or (−)-enantiomer.

18. The process according to claim 17 wherein the [R*NHOZ][HA*] salt is selected from the combinations of (+)(+), (+)(−), (−)(+) or (−)(−) entantiomers.

19. The process according to claim 13 wherein the diasteriomeric acid addition salt is (S)-N-(6-benzyloxy-2,3-dihydrobenzofuran-3-yl) hydroxylamine (S)-mandelate;
(R)-N-(6-benzyloxy-2,3-dihydrobenzofuran-3-yl) hydroxylamine (S)-mandelate;
(S)-N-(6-[2,6-difluoro-benzyloxy]-2,3-dihydrobenzofuran-3-yl)hydroxylamine (S)-mandelate;
(R)-N-(6-[2,6-difluro-benzyloxy]-2,3-dihydrobenzofuran-3-yl)-hydroxylamine (S)-mandelate;
(S)-N-(1-benzo[b]thien-2-yl-ethyl)hydroxylamine (S)-mandelate;
(R)-N-(1-benzo[b]thien-2-yl-ethyl)hydroxylamine (S)-mandelate;
(S)-N-(1-benzo[b]thien-2-yl-ethyl)hydroxylamine (R)-mandelate;
(R)-N-(1-benzo[b]thien-2-yl-ethyl)hydroxylamine (R)-mandelate;
(S)-N-(4-[5-(4-Fluorophenoxy)-2-furyl]-3-butyn-2-yl] hydroxylamine (S)-mandelate;
(R)-N-(4-[5-(4-Fluorophenoxy)-2-furyl]-3-butyn-2-yl] hydroxylamine (S)-mandelate;
(S)-N-(4-[5-(4-Fluorophenoxy)-2-furyl]-3-butyn-2-yl] hydroxylamine (R)-mandelate; or
(R)-N-(4-[5-(4-Fluorophenoxy)-2-furyl]-3-butyn-2-yl] hydroxylamine (R)-mandelate.

20. The process according to claim 13 wherein the diasteriomeric acid additions salts are separated by crystallization.

21. The process according to claim 20 wherein a suitable solvent for separation of the organic acid from the homochiral hydroxylamine is ethyl acetate or an alcohol; or a mixture thereof.

22. The process according to claim 21 wherein the alcohol is methanol or ethanol.

* * * * *